United States Patent [19]

Halloran et al.

[11] Patent Number: 5,085,858
[45] Date of Patent: Feb. 4, 1992

[54] THIOGLYCOLAMIDE-FUNCTIONAL SILOXANES

[75] Inventors: Daniel J. Halloran; Padmakumari J. Varaprath, both of Midland, Mich.

[73] Assignee: Dow Corning Corporation, Midland, Mich.

[21] Appl. No.: 667,122

[22] Filed: Mar. 11, 1991

Related U.S. Application Data

[62] Division of Ser. No. 462,185, Jan. 9, 1990, Pat. No. 5,068,378.

[51] Int. Cl.$^5$ .......................... A61K 7/09; A45D 7/04
[52] U.S. Cl. ......................................... 424/71; 132/203
[58] Field of Search ........................... 424/71, 72, 78; 132/203, 204, 209

[56] References Cited

U.S. PATENT DOCUMENTS

| | | | |
|---|---|---|---|
| 2,944,942 | 7/1960 | Charle et al. | 424/72 |
| 3,314,982 | 4/1967 | Koerner et al. | 252/8.57 |
| 3,660,454 | 5/1972 | Gornowiez et al. | 556/419 X |
| 3,812,164 | 5/1974 | Schulz | 556/419 X |
| 3,959,327 | 5/1976 | Pepe et al. | 528/27 X |
| 4,434,161 | 2/1984 | Barga | 556/419 X |
| 4,783,490 | 11/1988 | Eckberg et al. | 528/26 X |
| 4,933,414 | 6/1990 | Eckberg et al. | 528/26 |
| 4,973,475 | 11/1990 | Schnetzinger et al. | 514/772 X |

FOREIGN PATENT DOCUMENTS 1182939  4/1970  United Kingdom .
1199776  7/1970  United Kingdom .

*Primary Examiner*—Thurman K. Page
*Assistant Examiner*—Susan S. Rucker
*Attorney, Agent, or Firm*—Sharon K. Severance

[57] ABSTRACT

Disclosed are thioglycolamide functional siloxanes and their salts which are prepared from the reaction between an amine-functional siloxane and thioglycolic acid or a thioglycolic ester. These materials are useful as reducing agent in the perming process. They are also useful in conditioning the hair.

6 Claims, No Drawings

THIOGLYCOLAMIDE-FUNCTIONAL SILOXANES

This is a divisional of copending application(s) Ser. No. 07/462,185 filed on Jan. 9, 1990 now U.S. Pat. No. 5,068,378.

This invention pertains to thioglycolamide-functional siloxanes and their salts and methods for their preparation. The siloxanes of this invention are useful in the perming and conditioning of human hair. They may be used to replace typical thioglycolate solutions used in traditional perms.

BACKGROUND OF THE INVENTION

The process of perming hair consists of two essential steps. The first step is the breaking (reduction) of keratin disulfide (K-S-S-K) bonds in the hair to produce K-S-H functionality. The K-S-H groups are then oxidized in a curled state to produce new crosslinked K-S-S-K bonds. The typical agents for reducing the bonds are thioglycolate salts, which cause the strong odor associated with the perms. The typical agent for the oxidation of the bonds is hydrogen peroxide.

Mercapto-functional siloxanes and their use in the perming process of hair is known in the art. These materials usually contain a reactive —SH functional group on the end of the siloxane chain thereby making them useful substitutes for organic thioglycolates. Of the compounds known in the art the —SH functionality is attached directly on the silicon atom or it is attached to the silicon through an organic linkage consisting of carbon, hydrogen and optionally oxygen.

U.S. Pat. No. 2,944,942 to Charle et al. teaches methylsilyl mercaptoacetates that are useful in the permanent deformation of live hair and other analogous fibers. The —SH is attached to the silicon atom through an acetate linkage. These materials, as taught by Charle et al., are produced by the reaction between a methyl chlorosilane and an excess of an alkali metal thioglycolate. These materials, when used as a reducing agent, help protect and embellish while increasing the elasticity and luster of the hair.

U.S. Pat. No. 3,314,982 to Koerner et al. teaches the preparation of organosilicon compounds containing an alkyl mercapto group on the silicon atom. These compounds are formed through an alkaline cleavage reaction. In this instance the —SH functionality is attached to the silicon atom through an alkyl linkage comprised of at least 3 carbon atoms. Isothiuronium salt compounds, which are formed as an intermediate, are also described. Hair that has been treated with the materials taught by this invention is imparted with a permanent softness and can be easily styled and shaped.

British Patent No. 1,182,939 to Musolf teaches mercapto alkoxysilanes or siloxane polymers which are applied as an aqueous dispersion after the keratin disulfide linkages have been broken and prior to reoxidizing them. The —SH functionality may be directly attached to the silicon atom in this patent or attached through alkyl linkages. These compounds create water repellant properties on the hair as well as sheen and luster. The organosilicon compounds, as taught by Musolf, impart to the hair an improved body and sheen and a water resistant character.

British Patent No. 1,199,776 to McCarty et al. teaches the mercapto polysiloxanes that are chemically bonded into the hair. They are applied after reduction but prior to oxidation of the hair. The polysiloxanes are produced by equilibration reactions or by co-hydrolysis and condensation. The —SH functionality is attached to the silicon atom through an alkyl linkage. These compounds render the hair more attractive and provide a mechanism for protecting the hair against humidity caused effects.

The compounds of the instant invention are novel in that the —SH functionality is joined to the silicon atom through an amide-functional group. The presence of the amide groups and the thio functionality provide unique properties when used in hair waving or straightening.

The objects of this invention are novel thioglycolamide functional siloxanes and their salts and a method for their preparation.

It is also an object of this invention to use the thioglycolamide functional siloxanes in the perming and conditioning of human hair.

THE INVENTION

The compounds of this invention are referred to as thioglycolamide functional siloxanes and their salts. They are prepared from the reaction between an amine-functional siloxane or polysiloxane (herein referred to only as amine-functional siloxane(s)) and thioglycolic acid or thioglycolic acid derivatives (herein referred to only as thioglycolic acid), forming a salt, with subsequent dehydration to form the thioglycolamide functional siloxane. They can also be prepared by the reaction between the amine functional polysiloxanes and a thioglycolic ester or a derivative of a thioglycolic ester (herein referred to only as a thioglycolic ester).

The compounds of this invention can be prepared from amine functional siloxanes that are commercially available or prepared by known methods. The amine functional siloxanes useful in this invention may be polymers or copolymers that are linear or cyclic in structure. It is preferred that primary amine-functional siloxanes be used, however, secondary amine-functional siloxanes can also be used.

The cyclic amine functional siloxanes useful in this invention are selected from the groups comprising

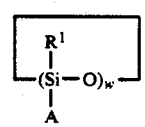   (I)

and

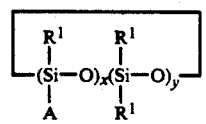   (II)

wherein each $R^1$ independently selected from an alkyl group containing 1 to 6 carbon atoms, and an aryl group containing 6 to 10 carbon atoms; each A is independently selected from $R^1$ and an amine functional group with the provision that at least one A group be an amine-functional group; w has the value of 3 to 6; x has the value of 1 to 6 and y has the value of 1 to 6; with the provision that the sum of x+y equals at least 3. The preferred cyclic structure is when $R^1$ is a methyl or phenyl group.

The linear amine functional siloxanes useful in this invention are selected from the groups comprising

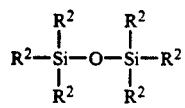 (III)

and

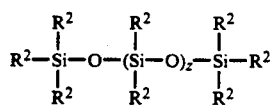 (IV)

wherein each $R^2$ is independently selected from A and $R^1$ with the provision that at least one $R^2$ group be an amine functional group; and z has the value of 1 to 10. It is feasible to use amine functional compounds in which z has the value of greater than 10 to produce thioglycolamide functional siloxanes, however, the resulting thioglycolamide functional siloxanes produced from amine functional siloxanes in which z is greater than 10 are not useful in the perming of hair. When $R^2$ is not an amine functional group it is preferred that $R^2$ be a methyl or phenyl group.

The amine functional group can be further exemplified by the formula

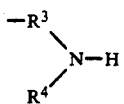 (V)

wherein each $R^3$ is independently selected from a straight or branched chain alkylene group consisting of 1 to 6 carbon atoms; $R^4$ is selected from the hydrogen atom, a straight or branched chain alkyl group consisting of 1 to 6 carbon atoms, and the group $—R^3—N(R^5)—H$; and $R^5$ is selected from $R^1$, and the hydrogen atom. The amine-functional groups can comprise primary and secondary mono or diamines and mixtures thereof.

The amine functional group can be further exemplified by, but not limited to, the following structures

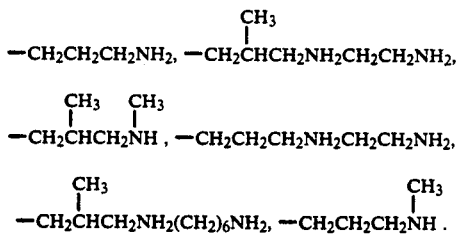

The amine-functional siloxanes used to produce thioglycolamide functional siloxanes useful in hair perming and conditioning can comprise mixtures of components varying in molecular weight and/or structures or they can comprise a single component. Compounds of the formulas (I-IV) in which x, y, and z are larger than the values stated above can be contained in the mixtures or single components as impurities. However, it is preferred that the mixture or single component be comprised essentially of the components described above by formulas (I-IV) for use in hair perming and conditioning.

The amine functional siloxanes of formulas (I-IV) are reacted with thioglycolic acid of the general formula

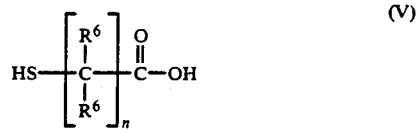 (V)

where each $R^6$ is independently selected from the hydrogen atom, $R^1$ and the group $—NH_2$; and n has the value of 1 to 6. It is preferred to use at least one mole of thioglycolic acid for every mole of amine contained in the compound. For example if a diamine is present, such as $—NH—CH_2—CH_2—NH_2$, at least two moles of thioglycolic acid should be used so that each amine contains the thioglycolic functionality after the reaction is complete. However, with diamines, it may be desirable to leave some unreacted amine in the reaction product. This can be accomplished by using less than the molar equivalents of thioglycolic acid or thioglycolic ester which is required to provide a complete reaction. An excess of the thioglycolic acid can be used to ensure reaction on every amine group.

The reaction between the thioglycolic acid and the amine functional siloxane can be initiated at room temperature and the reaction is exothermic. Temperatures above and below room temperature may also be suitable for initiation of the reaction. It preferred to keep the initiation and reaction temperature below the boiling point of the raw materials. It is also preferable to carry out the reaction at atmospheric pressure but pressures that are higher or lower than atmospheric are also useful.

It is also feasible to carry out the reaction in the presence of a solvent. It is preferred that the solvent be semi-polar organic or a low molecular weight silicone. It is also preferred that the solvent contain no active hydrogen atoms. Preferred solvents for the reaction include toluene, xylene, tetrahydrofuran, dimethoxyethane, methyl cellusolve, dimethyl ether of diethylene glycol, 1,2 dimethoxyethane, dimethicone cyclomethicone and others.

Water is produced as a by product of the reaction between the amine-functional siloxane and the thioglycolic acid and is removed from the reaction mixture to form the thioglycolamide functional siloxane. Prior to removal of the water, the reaction mixture comprises the salt of the thioglycolic acid and the amine functional siloxane. The water can be removed from the reaction mixture by subjecting the reaction mixture to heat and optionally reducing the pressure. Temperature at which the solvent refluxes or the water boils is usually sufficient to remove the water. The water can also be removed by azeotropes.

The thioglycolamide functional siloxanes produced by the reaction described above can be represented by the general formulas

 (VI)

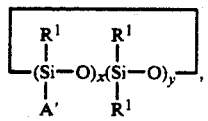

(VII)

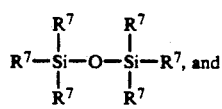

(VIII)

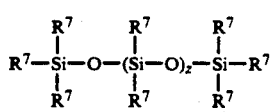

(IX)

and mixtures thereof;
wherein $R^1$ is as described above; $A'$ is independently selected from $R^1$ and a thioglycolamide functional group with the provision that at least one $A'$ group be a thioglycolamide functional group; $R^7$ is independently selected from $A'$ and $R^1$ with the provision that at least one $R^7$ group be the thioglycolamide functional group; w has the value of 3 to 6; x has the value of 1 to 6; y has the value of 1 to 6; and z has the value of 1 to 10; with the provision that the sum of x+y equals at least 3.

The thioglycolamide functional group can be further exemplified by the general formula

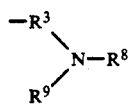

(X)

wherein $R^3$ is as described above; $R^8$ is selected from the hydrogen atom and the thioglycol functional group; $R^9$ is selected from the hydrogen atom, a straight or branched chain alkyl group consisting of 1 to 6 carbon atoms, and the group $-R^3-N(R^{10})-H$; and $R^{10}$ is selected from $R^1$ and $R^8$;
with the provision that at least one of the $R^8$ and/or $R^{10}$ groups is the thioglycol functional group.

The thioglycol functional group is represented by the general formula

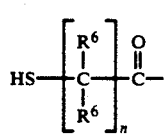

(XI)

where $R^6$ is as described above.

Salts of the thioglycolamide functional siloxanes are formed as an intermediate in the process of forming the thioglycolamide functional siloxanes and may be isolated in a stable form. The salts of the siloxanes are the products formed prior to the removal of any water or subjecting the reaction mixture to heat other than that produced by the exotherm. The structure of the thioglycolamide salt may be further exemplified, for example on a primary amine, by

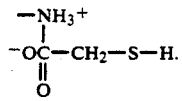

(XII)

An alternative method for making the thioglycolamide functional siloxanes comprises reacting a thioglycolic ester or a thioglycolic ester derivative with the amine functional siloxanes of formulas (I-IV) in the presence of heat and a catalyst. This alternative route will not form the salts as an intermediate product but will result directly in the formation of the thioglycolamide functional siloxanes.

The thioglycolic ester and derivatives can be exemplified by the following general formula

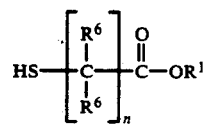

(XIII)

where $R^1$ and $R^6$ are as described above.

The reaction requires the use of a catalyst and heat for the reaction to proceed. Catalysts suitable for the reaction between the thioglycolic ester and the amine functional siloxane include acids such as mineral acids, sulfonic acids, strong cation exchange resins and others or bases such as sodium methoxide, strong anion exchange resins and others. Temperatures for carrying out the reaction should be maintained between 30° and 100° C. The preferred catalyst for the reaction is the basic type such as sodium methoxide. The preferred temperature for carrying out the reaction is between 50° C. and 80° C.

The typical procedure for carrying out the reaction between the amine-functional siloxane and the thioglycolic ester includes mixing the amine functional siloxane and the catalyst, adding the thioglycolic ester to the mixture, heating the mixture and holding at the desired temperature until the reaction has completed. It may be further desirable to neutralize the catalyst upon completion of the reaction by, for example, adding an acid to the reaction mixture when a base catalyst has been employed. For, example small quantities of acetic acid may be added to the reaction mixture to neutralize a sodium methoxide catalyst.

An alcohol is produced as a by-product of the reaction between the thioglycolic ester and the amine functional siloxane. The alcohol can be removed from the reaction product by further subjecting the reaction product to heat and optionally reduced pressure. Some alcohols may also be removed from the reaction product as it is being formed by allowing the temperature in the reaction zone to be higher than the boiling point of the alcohol being formed but below the boiling point of the raw materials.

The reaction can be carried out in the presence of a solvent. The solvents described above useful for the reaction between the thioglycolic acid and the amine functional siloxane are also useful in the reaction between the thioglycolic ester and the amine functional siloxane. The solvent can be removed after the reaction has been completed by further subjecting the reaction mixture to heat and optionally reduced pressure.

The thioglycolamide siloxanes of this invention, preferably those represented by formula (IX), are useful in the perming and conditioning of hair and can be applied to the hair using a suitable delivery system. Solvents, in particular alcohols, are one example of a suitable delivery system. It may also be useful to apply them from delivery systems such as water, low molecular weight alkanes, silicones, isoparafins and others.

For application to the hair it is preferable to use solutions in which the thioglycolamide functional siloxane comprises 1 to 50% of the total solution by weight. The more preferred range is for the thioglycolamide siloxane to comprise 20 to 40 percent by weight of the total solution. Solutions are prepared by mixing together the thioglycolamide functional siloxane and the delivery system. Compatabilizers, surfactants, and dispersing aids may be necessary to ensure a homogeneous mixture of the thioglycolamide functional siloxane and the delivery system.

It is preferred that the thioglycolamide siloxanes of the instant invention have a molecular weight of less than 1000 and more preferably of less than 500 for use on hair. The lower molecular weight materials are preferred so that they may diffuse into the hair, which is wound onto curling rods, in a relatively short period time. The resulting thioglycolamide siloxanes may contain a small amount of higher molecular weight materials (greater than 1000) introduced by impurities in the amine-functional siloxanes. These materials should only comprise a small amount of the total composition and the remainder should be comprised essentially of the lower molecular weight thioglycolamide materials.

The thioglycolamide siloxanes of this invention can be used in place of typical reducing agents in the curling of hair. The typical process for using the thioglycolamide siloxanes comprises washing and setting the hair by normal methods. The thioglycolamide siloxane is applied evenly on the hair. The treated hair is then allowed to stand at room temperature or in the presence of heat for a period sufficient to produce the desired curl. The hair is then water washed and treated with an oxidizing agent known in the art. The most typical oxidizing agent is an aqueous solution of hydrogen peroxide. After oxidation the hair is then rinsed with water and styled in the desired manner.

It is theorized that the following reaction takes place on the hair when using the thioglycolamide functional siloxanes of this invention

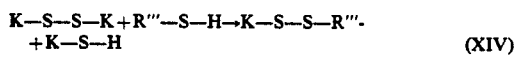

+K—S—H            (XIV)

where R'''—S—H represents the thioglycolamide functional siloxane. Thus an amide-functional siloxane is incorporated into the hair structure during the process of reduction. It is further theorized that this incorporation of the siloxane into the hair is the means for imparting some conditioning effect to the hair. Thus the thioglycolamide functional siloxanes of this invention are useful in the reduction of hair while simultaneously imparting some conditioning effects.

The thioglycolamide siloxanes of this invention, when used in the reduction of hair, are lower in odor than those that are currently commercially available for the reduction of hair. They produce a curl which is at least equal to that produced by typical reducing agents such as thioglycolic acid or thioglycolates. In addition the thioglycolamide siloxanes of this invention impart improved settability of the treated hair as well as the above mentioned conditioning effects.

The salts of the thioglycolamide functional siloxanes are also useful in the perming and conditioning of hair.

So that those skilled in the art can understand and appreciate the invention taught herein, the following examples are presented, it being understood that these examples should not be used to limit the scope of this invention over the limitations found in the claims attached hereto.

PREPARATION OF AMINE-FUNCTIONAL SILOXANES

Example A

Preparation of

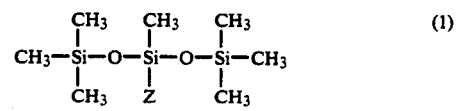

where Z is —CH$_2$—CH(CH$_3$)—CH$_2$—NH—CH$_2$—CH$_2$—NH$_2$.

A flask was equipped with a nitrogen source, thermometer, stirrer, and a Dean-Stark trap and reflux condenser. The flask was purged with nitrogen and maintained under a nitrogen blanket during the entire operation. 309.5 grams of a mixture of (CH$_3$—Si(Z)—O)$_b$, where b equals 3 to 6, was placed in the flask with 400.5 grams of reagent grade xylene and 17.5 grams of potassium silanolate catalyst.

Heat was applied until a temperature of 141° C. was achieved. The reaction mixture was held at approximately 141° C. for a period of 1.5 hours during which time the xylene was refluxing. 2.7 grams of water and 18 grams of an unidentified hazy material were removed. The reaction product was stripped at 80° to 132° C. and 50 to 3 torr.

934.7 grams of hexamethyldisiloxane was added to the stripped reaction mixture. Heat was applied for 12 hours maintaining a temperature between 97.5° and 106.5° C. 1.8 grams of acetic acid and 10.4 grams of Hiflo Supercell filter aid were added. The mixture was agitated for 30 minutes and filtered. The reaction product was comprised of 39.6% (Gas Chromatograph (GC) Area %) of the material of formula (1), 46.8% of hexamethyldisiloxane, and 13.6% of other reaction by-products and xylene.

Example B

The reaction product of example A was stripped at atmospheric pressure and 97° to 100° C. The resulting product was 71.5% (Gas Chromatograph (GC) Area %) of the composition of formula (1), 12.6% hexamethyldisiloxane and 15.9% of other reaction products and xylene. Amine Neutral Equivalents (ANE) was measured to be 170.

Example C

Preparation of

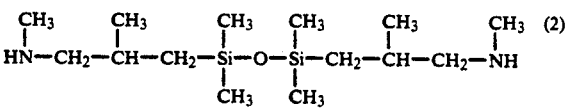

Using the same equipment as in example A, 1102.3 grams

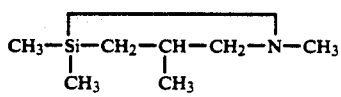

and 228 grams of reagent grade toluene were placed in the flask under a nitrogen blanket. 509 grams of deionized water was added over a period of 1 hour. The reaction temperature exothermed from 23° C. to 115° C. The contents were refluxed at 95° C. for 45 minutes after the water addition was complete. The water phase was separated off. The siloxane/toluene phase was heated to 95° to 140° C. removing an additional 50 grams of water. The reaction product was stripped at 23° to 50° C. and 7 torr. GC indicated 99 area % pure disiloxane of formula 2.

Example D

Preparation of

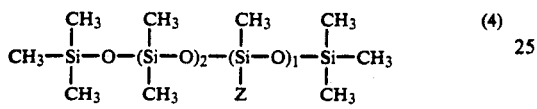

where Z is as described above.

359.4 grams of a mixture of $(CH_3-Si(Z)-O)_b$, where b equals 3 to 6 and Z is as described above was place in the flask with 640.6 grams of decamethyldisiloxane and 1.25 grams of potassium hydroxide (KOH). The mixtures was heated to 137° C. for and held for 5 hours. 4.1 grams of acetic acid was then added. The reaction mixture was stripped at 140° C. and 10 mm Hg for 2 hours and then filtered. Amine Neutral Equivalents were measured to be 190.9.

Example E

Preparation of

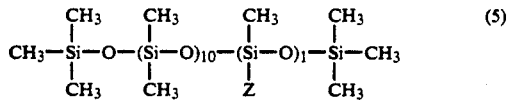

Using the same procedure as in example D the material of formula 5 was produced. The reactants were 161.7 of the amine used in example D, 288.1 grams of decamethyldisiloxane, 550.2 grams of a dimethyl cyclic siloxane mixture and 0.62 grams KOH. Following reaction at 135° C. for 5 hours, 1.02 grams of acetic acid and 10 grams additional cyclics were added. The product was stripped at 140° C. and 10 mm Hg for 2 hours. Amine Neutral Equivalents was measured to be 458.5.

PREPARATION OF THIOGLYCOLAMIDES

Example 1

206.7 grams of the amine-functional siloxane produced in example A was placed in a flask equipped with a nitrogen source, thermometer, stirrer and reflux condenser with a Dean-Stark trap. 51.3 grams of thioglycolic acid was added to the flask over a period of one hour while under a nitrogen blanket. A slight exotherm was observed. 128.3 grams of hexamethyldisiloxane was added and the mixture was heated to refluxed for 4 hours. About 4.4 grams of water and 12.5 grams of hazy material was removed. The reaction product was two phases, a clear liquid top and white paste bottom. The top phase was decanted.

200.0 grams of absolute ethanol was added to the paste produced above. The mixture was heated to reflux and a clear homogeneous fluid formed in a few minutes.

Example 2

67.92 grams of the product produced in example B as 112.8 grams of reagent grade toluene was placed in the flask used in example 1. 37.4 grams of thioglycolic acid was added dropwise for a period of 105 minutes. A slight exotherm was observed. The reaction mixture was heated to reflux and held for 4.75 hours. Approximately 5.5 grams of water and 15.0 grams of a hazy material were removed. A two phase product resulted. The top phase was decanted. The bottom phase was an thick orange paste.

· 102.0 grams of ethanol was added to the paste produced above. The mixture was heated to a light reflux and held for 15 minutes. The product was a clear homogeneous fluid, golden colored.

EXAMPLE 3

95.4 grams of the material produced in example D and 122.3 grams of reagent grade toluene were placed in a flask. 46.0 of thioglycolic acid and 32.1 grams of toluene were mixed and added dropwise into the flask over a period of 10 minutes. A slight exotherm was observed. The mixture was heated to toluene reflux for 5 hours. A total of 6.9 grams of water was removed. The resulting mixture was two phases. The top phase was decanted. The bottom phase was an orange paste.

EXAMPLE 4

Using the same procedure as in example 3, the thioglycolamide was produced from the material in Example E. The reactants were 119.4 grams of the amine prepared in example E, 61.2 grams of toluene (in pot), 23.93 grams TGA and an additional 41.2 grams toluene (with TGA). A two phase product resulted. The product was distilled at 38° to 40° C. and 30 torr. A red-/orange opaque hazy fluid resulted.

EXAMPLE 5

81.29 grams of the material produced in Example C and 70.4 grams of xylene were placed in the flask. 49.7 grams of thioglycolic acid was added dropwise over a period of 20 minutes. An exotherm of 23° to 60° C. was observed. The mixture was heated to xylene reflux and held for 3.5 hours. Approximately 9.2 grams of water was removed. The cooled product was a light-green, slightly hazy, low viscosity fluid.

EXAMPLE 6

Preparation of Salts:

10.0 grams of the amine prepared in example D, 27.5 grams toluene and 4.8 grams TGA were mixed in a 4 oz. bottle. A clear homogeneous fluid resulted.

10 grams of the amine prepared in example C, 39 grams toluene and 6.04 grams TGA were mixed in a 4 oz. bottle. A clear homogeneous fluid resulted.

EXAMPLE 7

30 grams of the amine functional siloxane prepared in Example B, 100 grams of toluene and 2.0 grams of 25% solution of sodium methoxide in methanol was placed in a flask equipped with a distilling head and drop funnel. 15 grams of methyl thioglycolate was added gradually from the drop funnel into the flask contents while stirring. The mixture was heated to 60° to 80° C. for 5 hours. The reaction mixture was cooled and acetic acid was added to neutralized the sodium methoxide catalyst. The solvent was removed under heat and reduced pressure.

EXAMPLE 8

30 grams of the amine functional siloxane prepared in Example C, 100 grams of toluene and 2.0 grams of 25% solution of sodium methoxide in methanol was placed in a flask, in that order, equipped with a distilling head and drop funnel. 15 grams of methyl thioglycolate was added gradually from the drop funnel into the flask contents while stirring. The mixture was heated to 60° C. for 5 hours. The reaction mixture was cooled and acetic acid was added to neutralized the sodium methoxide catalyst. The solvent was removed under heat and reduced pressure.

EXAMPLE 9

Two (A and B), 2 gram, European Brown, tresses of virgin human hair were shampooed and rolled onto standard perming rods.

Tress A was treated with 10 grams of ammonium thioglycolate acid solution (pH=9 to 9.5), covered and placed in a 40° C. oven for 30 minutes.

Tress B was treated with 10.1 grams of a solution consisting on 15.3 grams of the material produced in example 1, 1.00 gram of concentrated ammonium hydroxide solution and 91.65 grams of water. The solution had a pH of 9 to 9.5. The hair was covered and placed in a 40° C. oven for 30 minutes.

Both tresses were rinsed under running water for 2 minutes, saturated with a 2.2% hydrogen peroxide solution and allowed to stand in the peroxide solution for 5 minutes. The rods were then removed, the hair rinsed with fresh 2.2% hydrogen peroxide solution for 2 minutes followed by placing them under running water for approximately 30 seconds and hanging them to dry for 24 hours. Tress B has a curl equivalent to that of tress A.

What is claimed is:

1. A hair treating composition comprising
(A) a thioglycolamide functional siloxane of the formula

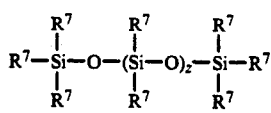

and
(B) a delivery means;
wherein each $R^7$ is independently selected from the groups consisting an alkyl group containing 1 to 6 carbon atoms, an aryl group containing 6 to 10 carbon atoms, and a thioglycolamide functional group having the formula:

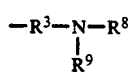

where each $R^3$ is independently selected from a straight or branched chain alkylene group consisting of 1 to 6 carbon atoms;
$R^8$ is selected from the group consisting of the hydrogen atom and a thioglycol functional group having the general formula

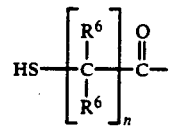

where each $R^6$ is independently selected from the groups consisting of the hydrogen atom, an alkyl group containing 1 to 6 carbon atoms, an aryl group containing 6 to 10 carbon atoms, and the group $NH_2$ and n has the value of 1 to 6;
$R^9$ is selected from the group consisting of the hydrogen atom, a straight or branched chain alkyl group consisting of 1 to 6 carbon atoms and the group $—R^3—N(R^{10})—H$,
where $R^{10}$ is selected from the group consisting of $R^8$, an alkyl group containing 1 to 6 carbon atoms, an aryl group containing 6 to 10 carbon atoms; with the provision that at least one of the $R^8$ or $R^{10}$ groups is the thioglycol functional group;

with the provision that at least one $R^7$ group be a thioglycolamide functional group, and z has the value of 1 to 10.

2. A method of treating hair comprising applying the composition as claimed in claim 1 to the hair.

3. A hair treating composition comprising
(A) a thioglycolamide functional siloxane of the formula

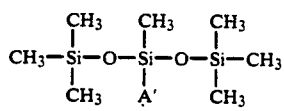

wherein A' is

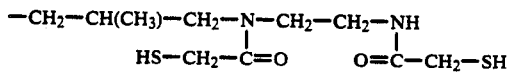

and
(B) a delivery means.

4. A method of treating hair comprising applying the composition as claimed in claim 3 to the hair.

5. A hair treating composition comprising
(A) a salt of a thioglycolamide functional siloxane selected from cyclic siloxanes having the formulas

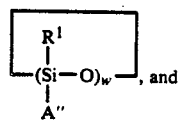, and

-continued

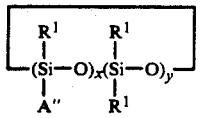

and linear siloxanes having the formulas

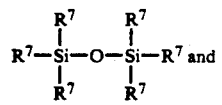

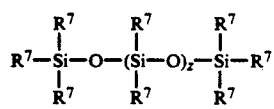

and mixtures thereof;
and
(B) a delivery means
wherein each $R^1$ is independently selected from the groups consisting of an alkyl group containing 1 to 6 carbon atoms, and an aryl group containing 6 to 10 carbon atoms; each $A''$ is independently selected from the group consisting of $R^1$ and a salt of a thioglycolamide functional group having the formula

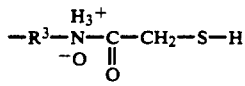

where each $R^3$ is independently selected from a straight or branched chain alkylene group consisting of 1 to 6 carbon atoms;
with the provision that at least one $A''$ group be a salt of a thioglycolamide functional group;
each $R^7$ is independently selected from the groups consisting of $A''$ and $R^1$ with the provision that at least one $R^7$ group be a salt of a thioglycolamide functional group;
w has the value of 3 to 6;
x has the value of 1 to 6;
y has the value of 1 to 6; and
z has the value of 1 to 10; with the provision that the sum of $x+y$ equals at least 3.

6. A method of treating hair comprising applying the composition as claimed in claim 5 to the hair.

* * * * *